(12) United States Patent
Gallily et al.

(10) Patent No.: US 11,149,014 B2
(45) Date of Patent: Oct. 19, 2021

(54) METHOD FOR TREATING PAIN OR ASSOCIATED CONDITION OR SYMPTOM

(71) Applicant: Yissum Research Development Company of the Hebrew University of Jerusalem Ltd., Jerusalem (IL)

(72) Inventors: Ruth Gallily, Jerusalem (IL); Raphael Mechoulam, Jerusalem (IL); Aviva Breuer, Jerusalem (IL)

(73) Assignee: Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 204 days.

(21) Appl. No.: 16/274,107

(22) Filed: Feb. 12, 2019

(65) Prior Publication Data

US 2019/0169148 A1    Jun. 6, 2019

Related U.S. Application Data

(60) Division of application No. 15/821,720, filed on Nov. 22, 2017, now Pat. No. 10,239,848, which is a division of application No. 15/293,155, filed on Oct. 13, 2016, now abandoned, which is a continuation of application No. PCT/IL2015/050420, filed on Apr. 21, 2015.

(60) Provisional application No. 61/981,997, filed on Apr. 21, 2014.

(51) Int. Cl.
  *C07D 295/15*  (2006.01)
  *A61K 31/215*  (2006.01)
  *A61K 31/5375*  (2006.01)

(52) U.S. Cl.
  CPC .......... *C07D 295/15* (2013.01); *A61K 31/215* (2013.01); *A61K 31/5375* (2013.01)

(58) Field of Classification Search
  CPC ... A61K 31/215; A61K 31/5375; A61P 25/04; A61P 29/00; A61P 3/00; A61P 3/04; C07D 295/15
  See application file for complete search history.

(56) References Cited

FOREIGN PATENT DOCUMENTS

| GB | 2439393 | * 12/2007 | |
|---|---|---|---|
| WO | WO 2007/138322 | 12/2007 | |
| WO | WO 2008/107879 | 9/2008 | |
| WO | WO-2008107879 A1 | * 9/2008 | ............. C07C 43/23 |
| WO | WO 2009/018389 | 2/2009 | |

OTHER PUBLICATIONS

International Search Report issued in application No. PCT/IL2015/050420 dated Jul. 7, 2015.
Bulló-Bonet et al; "Tumour necrosis factor, a key role in obesity?" FEBS Letters vol. 451, No. 3, pp. 215-219. (1999).
Extended European Search Report (EESR) received in European Patent Application No. 202001781.0 dated Jan. 26, 2021.

* cited by examiner

*Primary Examiner* — Umamaheswari Ramachandran
(74) *Attorney, Agent, or Firm* — Knobbe, Martens, Olson & Bear, LLP

(57) ABSTRACT

Compositions that include certain phenyl substituted cyclohexenyl compounds are administered to a subject in a method for treating obesity or an associated disease or disorder or in a method of reducing food consumption or body weight.

12 Claims, 11 Drawing Sheets

METHOD FOR TREATING PAIN OR ASSOCIATED CONDITION OR SYMPTOM

INCORPORATION BY REFERENCE TO ANY PRIORITY APPLICATIONS

Any and all applications for which priority claims are identified in the application data sheet, or any correction thereto, are hereby incorporated by reference, including the claim that this application is a divisional of U.S. application Ser. No. 15/821,720, filed Nov. 22, 2017, which is a divisional of U.S. application Ser. No. 15/293,155, filed Oct. 13, 2016, now abandoned, which is the continuation of International Application No. PCT/IL2015/050420 filed Apr. 21, 2015, which claims the benefit of U.S. Provisional Application No. 61/981,997 filed Apr. 21, 2014.

BACKGROUND OF THE INVENTION

Field of the Invention

This invention relates to phenyl substituted cyclohexenyl compounds, compositions comprising them and uses thereof for the preparation of medicaments.

Description of the Related Art

Cannabidiol (CBD), a constituent of Cannabis sativa, is the major non-psychotropic cannabinoid. CBD has been shown in in vitro assays, as well as in in vivo assays to produce numerous pharmacological effects, some of which are of high potential therapeutic value. For example, effects of CBD were associated with the treatment of neurological diseases, anxiety and psychosis. CBD was also found to be a neuroprotective antioxidant. The in vitro effects of CBD on immune cells was also shown, such as the inhibition of nitric oxide (NO) production by mouse peritoneal macrophages and the suppression of TNF—α, IL-1a and IFNγ by human peripheral blood mononuclear cells. These in vitro studies lend support to earlier reports on analgesic and anti-inflammatory effects of CBD in animals.

CBD was also shown to have very limited anti-obesity effect. Ignatowska-Jankowska et al. (*Neurosci Lett.* 2011, 490, 82-4) have shown that CBD decreases body weight gain in rats through involvement of CB2 receptors. However, Scopinho et al., (*Pharmacol Biochem Behav.* 2011, 98, 268-272) report that CBD did not change food intake in fed or fasted rats.

SUMMARY OF THE INVENTION

In the first of its aspects the invention provides a compound of general formula (I), including any salt, enantiomer, diastereomer or mixtures thereof:

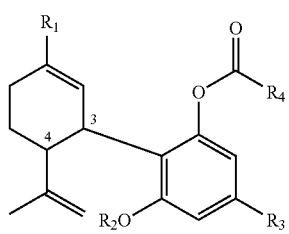

wherein
$R_1$, $R_2$ and $R_3$ are each independently selected from a straight or branched $C_1$-$C_{10}$ alkenyl or $C_2$-$C_{10}$ alkynyl; each independently optionally substituted by at least one substituent selected from hydroxy and halogen.

$R_4$ is a straight or branched $C_1$-$C_{10}$ alkyl, $C_2$-$C_{10}$ alkenyl or $C_2$-$C_{10}$ alkynyl, which is substituted by at least one substituent of general formula (II):

wherein
X is selected from N, $N^+H$, $N^+(C_1$-$C_{10}$ alkyl), $O^+$, $S^+$, P, $P^+H$;

$R_5$ and $R_6$ are each independently selected from H, $C_1$-$C_{10}$ alkyl, $C_2$-$C_{10}$ alkenyl or $C_2$-$C_{10}$ alkynyl; or both $R_5$ and $R_6$ together with X may form a $C_3$-$C_8$ heterocyclic ring;

wherein $R_5$ and $R_6$ may each independently be optionally interrupted by at least one heteroatom selected from —O—, —NH—, —S—, $N^+(C_1$-$C_{10}$alkyl);

The term "$C_1$-$C_{10}$alkyl" should be understood to encompass a saturated, branched or straight hydrocarbon group having from 1 to 10 carbon atoms. Typical $C_1$-$C_{10}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_1$-$C_6$-alkylene" as used herein represent a saturated, divalent, branched or straight hydrocarbon group having from 1 to 6 carbon atoms. Typical $C_1$-$C_6$-alkylene groups include, but are not limited to, methylene, ethylene, 1,2-propylene, 1,3-propylene, butylene, isobutylidene, pentylene, hexylene and the like.

The term "$C_2$-$C_{10}$ alkenyl" should be understood to encompass a branched or straight hydrocarbon group having from 2 to 10 carbon atoms and at least one double bond. Examples of such groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl and the like.

The term "$C_2$-$C_6$-alkenylene" as used herein represent a divalent, branched or straight hydrocarbon group having from 2 to 6 carbon atoms and at least one double bond. Typical $C_2$-$C_6$-alkenylene groups include, but are not limited to, ethenylene, n-propenylene, butenylene, pentenylene, hexenylene and the like.

The term "$C_2$-$C_{10}$ alkynyl" should be understood to encompass a branched or straight hydrocarbon group having from 2 to 10 carbon atoms and at least one triple bond. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

The term "$C_2$-$C_6$-alkynylene" as used herein represent a divalent, branched or straight hydrocarbon group having from 2 to 6 carbon atoms and at least one triple bond. Typical $C_2$-$C_6$-alkynylene groups include, but are not limited to, ethynylene, n-propynylene, butynylene, pentynylene, hexynylene and the like.

The term "optionally substituted by at least one substituent" should be understood to encompass selected from hydroxyl (—OH), halogen (selected from —F, —Cl, —Br, —I).

In some embodiments, X is selected from N and N$^+$H. In further embodiments, X is N$^+$H.

In some embodiments, R$_5$ and R$_6$ are each independently selected from H, C$_1$-C$_{10}$ alkyl, C$_2$-C$_{10}$ alkenyl or C$_2$-C$_{10}$ alkynyl. In some other embodiments R$_5$ and R$_6$ are each independently selected from C$_1$-C$_{10}$ alkyl, C$_2$-C$_{10}$ alkenyl or C$_2$-C$_{10}$ alkynyl, each being further optionally interrupted by at least one heteroatom group selected from —O—, —NH—, —S—. When referring to an alkyl, alkenyl or alkynyl being "interrupted by at least one heteroatom" it should be understood to encompass said hydrocarbon chain being substituted by said heteroatom or group between any two carbon atoms of said hydrocarbon chain.

In some other embodiments both R$_5$ and R$_6$ form together with X a C$_3$-C$_8$ heterocyclic ring. Said heterocylic ring formed by both R$_5$ and R$_6$ together with X, comprises at least one heteroatom (i.e. substituent X forming said hetereocyclic ring). In some other embodiments said heterocylic ring formed by both R$_5$ and R$_6$ together with X, comprises at least two heteroatoms (i.e. substituent X forming said hetereocyclic ring and at least one other heteroatom originating from substituents R$_5$ and/or R$_6$, as defined hereinabove).

The invention also includes any salt of a compound of formula (I), including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

A compound of formula (I) comprises at least two stereogenic centers, i.e. at positions 3 and 4 of the cyclohexenyl ring. In an embodiment where a compound of formula (I) comprises at least two stereogenic center, the invention also includes any enantiomer of a compound of formula (I), or any mixtures thereof (including a racemic mixture and any non-racemic mixture of two enantiomers of a compound of formula (I)). In an embodiment where a compound of formula (I) comprises at least two stereogenic centers, the invention also includes any diastereomer of a compound of formula (I), or any mixtures thereof (including any diastereomeric mixture of a compound of formula (I)).

In yet further embodiments, R$_4$ is a straight or branched C$_1$-C$_5$ alkyl substituted by a substituent of the general formula (III):

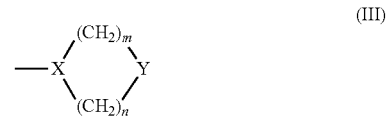

(III)

wherein m and n are each independently an integer selected from 0-5; wherein at least one of m or n is different than 0 (i.e. at least one of the integers m or n should be other than 0);

X is selected from N, N$^+$H, N$^+$(C$_1$-C$_{10}$ alkyl), O$^+$, S$^+$, P or P$^+$H;

Y is selected from —O—, —NH—, —N(C$_1$-C$_{10}$ alkyl)—, —S—, straight or branched C$_1$-C$_6$ alkylene, straight or branched C$_2$-C$_6$ alkenylene; straight or branched C$_2$-C$_6$ alkynylene.

In some embodiments m is equal to n. In other embodiments m and n are both 2, thereby a six membered ring of formula (III).

In some embodiments of general formula (III), X is selected from N and N$^+$H. In some other embodiments of general formula (III), Y is —O—.

In some embodiments of a compound of the invention, R$_1$ and R$_2$ are each independently a slight or branched C$_1$-C$_5$ alkyl.

In other embodiments of a compound of the invention R$_3$ is a slight or branched C$_4$-C$_{10}$ alkyl.

The compound of formula (I) comprises a cyclohexene ring, which under typical conditions will assume a chair conformation (or be in a steady state equilibrium of two possible chair conformations).

In further embodiments of a compound of the invention substituents on positions 3 and 4 of compound of general formula (I) have a cis configuration, i.e. the two substituents on positions 3 and 4 both pointing "up" or "down" from the mean plane of the ring. In other embodiments, the conformation of substituents on positions 3 and 4 of compound of general formula (I) are equatorial: axial or axial: equatorial (axial=substituent is positioned almost perpendicular to the mean plane; equatorial=substituent is positioned almost parallel to the mean plane.

In further embodiments of a compound of the invention, substituents on positions 3 and 4 of compound of general formula (I) have a trans configuration, i.e. the two substituents on positions 3 and 4 each pointing to two opposite directions from the mean plane of the ring (either substituent on position 3 is pointing "up" and substituent on position 4 is pointing "down" from the mean plane of the ring or substituent on position 3 is pointing "down" and substituent on position 4 is pointing "up" from the mean plane of the ring). In yet other embodiments of a compound of the invention, conformation of substituents on positions 3 and 4 of compound of general formula (I) are equatorial: equatorial or axial: axial.

In some embodiments the invention provides a compound of general formula (IV) including any salt, enantiomer, diastereomer or mixtures thereof:

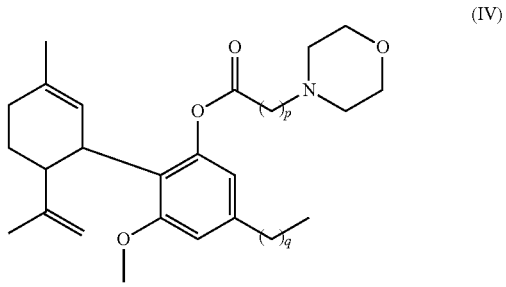

(IV)

wherein p and q are each independently an integer selected from 0-9. In some embodiments p is 2 and q is 4.

In some embodiments, the invention provides a salt of a compound of formula (IV), such as for example, a compound of general formula (V):

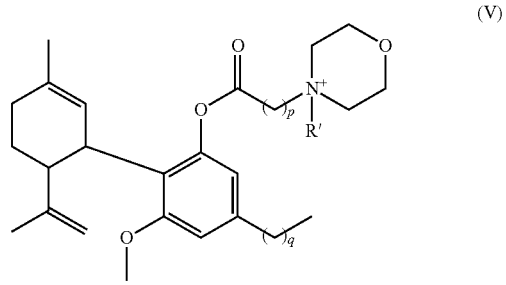

(V)

wherein p and q are each independently an integer selected from 0-9 and R' is H or a straight or branched $C_1$-$C_{10}$ alkyl; and wherein the counter ion is any pharmaceutically acceptable counter ion, such as for example maleate. In some embodiments, R' is H.

In some embodiments, a compound of the invention is substantially devoid of affinity to a CB receptor.

The term "substantially devoid of affinity to a CB receptor" refers to the capability of a compound of the invention to have an affinity to a cannabinoid (CB) receptor (i.e. the class of cell membrane receptors under the G protein-coupled receptor family which include the subtypes CB1 and CB2) of less than 2 µM (measured by the $K_i$ parameter of a compound to a CB receptor, therefore the $K_i$ of compounds of the invention is less than about 2 µM). Comparatively, THC which is the psychoactive component of cannabis, known to have binding affinity to CB1 receptor, has a binding $K_i$ of 66 nM.

In some embodiments, a compound of the invention is substantially devoid of affinity to a CB1 receptor or CB2 receptor. In other embodiments, a compound of the invention is substantially devoid of affinity to a CB1 receptor and CB2 receptor. Without being bound by theory it is stipulated that the substantial lack of affinity to a CB receptor provides a compound of the invention or a composition comprising a compound of the invention In another one of its aspects, the invention provides a compound of the invention for use as a medicament.

In a further aspect the invention provides a use of at least one compound of the invention, for the preparation of a medicament.

In some embodiments, said medicament is for the treatment of obesity and any disease or disorder associated therewith. In other embodiments, said medicament is for reduction in food consumption. In yet further embodiments, said medicament is for the reduction of body weight. In other embodiments, said medicament is for the treatment of inflammation and disorders associated therewith.

The term "treatment" as used herein means the management and care of a subject for the purpose of combating a disease, disorder or condition. The term is intended to include the delaying of the progression of a disease, disorder or condition, the alleviation or relief of symptoms and complications, and/or the cure or elimination of a disease, disorder or condition. A subject to be treated is preferably a mammal, in particular a human being.

The term "obesity and any disease or disorder associated therewith" should be understood to encompass a medical condition expressed in a subject by an excess in body fat to the extent that it may have an adverse effect on the general health of said subject, which may lead to several diseases and disorders associated with said condition.

Obesity treated by a compound or a composition of the invention may be caused by the following non-limiting conditions: excessive food consumption, lack of physical activity, genetic susceptibility, endocrine conditions or disorders, use of certain medications or psychiatric illness.

Obesity and an excess in body fact may be measured in a form known in the art, including direct measurements (including blood tests, MRI or CT measurements) or indirect measurements (including for example body mass index (BMI), which defines people as overweight (pre-obese) if their BMI is between 25 kg/m² and 30 kg/m², and obese when it is greater than 30 kg/m²).

It is noted that a compound or a composition of the invention may be used in combination with other known medicaments or methods such as for example other dietary supplements (from a natural or synthetic source), dieting and physical exercise. Said additional treatment may be performed prior, during or subsequent to the treatment of said subject with a compound or composition of the invention.

The term "reduction in food consumption" should be understood to encompass decrease in the intake of food in a subject treated with a compound or composition of the invention, of about 20-35% (in preferred embodiments from about 22 to about 35%) of corresponding food intake in said subject prior to the use of said compound or composition of the invention. Said reduction in food consumption may be achieved is said subject, either during the treatment of said subject with a compound or composition of the invention and/or subsequent to the treatment of said subject with a compound or composition of the invention.

The term "reduction of body weight" should be understood to encompass a decrease in the body weight of a subject treated with a compound or composition of the invention, of about 10-60% (in preferred embodiments from about 40 to about 60%) as compared with the body weight of said subject prior to the use of said compound or composition of the invention. Said reduction of body weight may be achieved is said subject, either during the treatment of said subject with a compound or composition of the invention and/or subsequent to the treatment of said subject with a compound or composition of the invention.

The term "abnormal food consumption" should be understood to encompass a condition in which a subject is consuming between 10% to 100% more food than the suggested nutritional diet typically recommended by health care givers (such as for examples doctors, dietitians, health regulators and so forth) considering the age and health of said subject (including parameters such as blood pressure, blood glucose levels, hormonal balance etc).

It should be understood that when treating obesity, abnormal food consumption, reducing food consumption, reducing body weight of a subject with a compound or composition of the invention, said treatment is characterized in having significant less psychiatric side effects, such as for example depression and anxiety episodes, upon short and long term use of said compound or composition of the invention.

The term "inflammation and disorders associated therewith" should be understood to encompass any inflammatory disease (either acute or chronic) in any part of a subject's body, and also conditions and disorders associated therewith.

In another one of its aspects the invention provides a composition comprising at least one compound of the invention.

In some embodiments a composition of the invention is for use in the treatment of obesity and any disease or disorder associated therewith. In some other embodiments a composition of the invention is for use in the reduction in food consumption. In other embodiments a composition of the invention is for use in the reduction of body weight. In further embodiments, a composition of the invention is for use in the treatment of inflammation and disorders associated therewith.

The present invention thus also relates to pharmaceutical compositions comprising at least one compound according to formula (I) in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy. Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered. In some embodiments of the invention a composition comprising a compound of the invention may include a dose ranging from 2-100 mg/Kg (range including a dose of 2, 4, 5, 10, 15, 20, 25, 30, 35, 40, 45, 50, 55, 60, 65, 70, 75, 80, 85, 90, 95, 100 mg/Kg).

In another aspect the invention provides a method of treating obesity and any disease or disorder associated therewith in a subject in need thereof, said method comprising administering to a subject in need thereof an effective amount of at least one compound of the invention.

In a further aspect the invention provides a method of reducing the food consumption of a subject in need thereof, said method comprising administering to a subject in need thereof an effective amount of at least one compound of the invention.

In a further aspect the invention provides a method of reducing the body weight of a subject in need thereof, said method comprising administering to a subject in need thereof an effective amount of at least one compound of the invention.

In another aspect the invention provides a method of treating inflammation and disorders associated therewith in a subject in need thereof, said method comprising administering to a subject in need thereof an effective amount of at least one compound of the invention.

As used herein, the term "effective amount" means that amount of a medicament, composition or compound of the invention administered will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

According to a further aspect the invention provides a compound of the invention, for use in the treatment of at least one disease, disorder or condition selected from obesity, abnormal food consumption and abnormal body weight, including any combinations thereof and conditions and symptoms associated therewith.

In a further aspect the invention provides a compound of the invention, for use in the treatment of at least one disease, disorder or condition selected from inflammation and pain, including any combinations thereof and conditions and symptoms associated therewith.

In another one of its aspects the invention provides a compound of the invention as described herein above, for use in the treatment of pain including any conditions and symptoms associated therewith.

The term "pain" should be understood to include any unpleasant sensory and emotional experience associated with actual or potential tissue damage, or described in terms of such damage. This term includes "acute pain", i.e. pain that in some conditions is transitory, lasting only until the noxious stimulus is removed or the underlying damage or pathology has healed. This term includes also "chronic pain". i.e. pain that persist for periods that extend beyond the removal of the noxious stimulus causing the pain initially. Such conditions include subjects that are suffering from diseases such as for example rheumatoid arthritis, peripheral neuropathy, cancer and idiopathic pain. Traditionally, the distinction between acute and chronic pain has relied upon an arbitrary interval of time from onset; the two most commonly used markers being 3 months and 6 months since the onset of pain, though some theorists and researchers have placed the transition from acute to chronic pain at 12 months. Others apply acute to pain that lasts less than 30 days, chronic to pain of more than six months duration, and subacute to pain that lasts from one to six months. Examples of type of pain include: nociceptive pain, neuropathic pain, phantom pain, psychogenic pain, breakthrough pain and incident pain.

When referring to the treatment of pain, it should be understood to encompass any qualitative or quantitative reduction in pain condition of a subject, including amelioration, reduction in sensation of pain (temporary or permanent), including any symptom associated therewith.

In some embodiments said pain is chronic pain.

The invention further provides a method of treating pain in a subject in need thereof, comprising administering to a subject in need thereof an effective amount of at least one compound of the invention.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF THE PREFERRED EMBODIMENT

Figure 1:
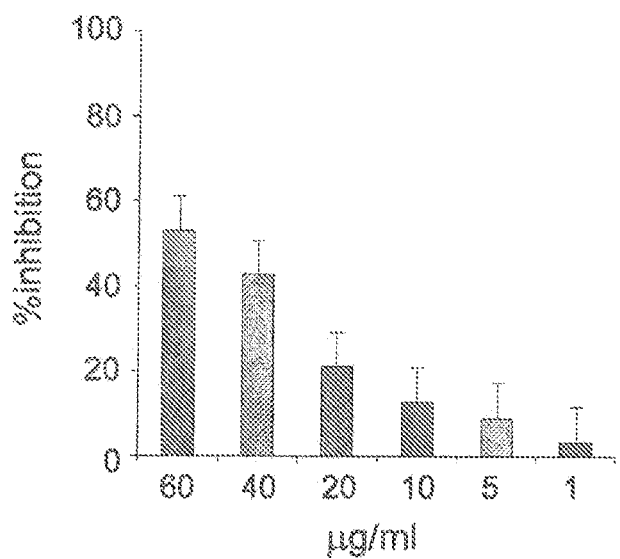
FIG. 1 shows the NO inhibition of RAW 264.7 macrophages treated with doses of 1-60 μg/ml of HU-436.

Preparation of 3-methoxy-2-((6R)-3-methyl-6-(prop-1-en-2-yl)cyclohex-2-enyl)-5-pentylphenyl 3-morpholinopropanoate (HU-435)

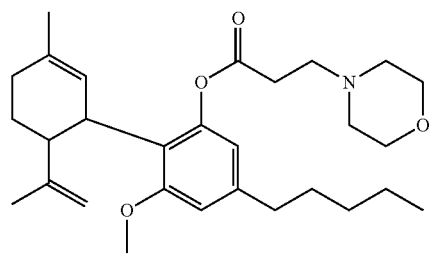 [SMILES: C=C(C)C1CCC(C)=CC1c1c(OC)cc(CCCCC)cc1OC(=O)CCN1CCOCC1]

3-Methoxy-2-((6R)-3-methyl-6-(prop-1-en-2-yl)cyclohex-2-enyl)-5-pentylphenyl 3-morpholinopropanoate (HU-435) was prepared from plant-derived cannabidiol which was converted to mono-methoxy CBD. Dicyclohexylcarbodiimide (DCC, 3.2 mmoles) was added to 4-morpholino propionic acid (3.2 mmoles), mono-methoxy CBD (1.6 mmoles) and pyrrolidinopyridine (0.32 mmoles) in dry $CH_2Cl_2$ (20 ml). The reaction mixture was stirred at room temperature overnight (precipitation of dicyclohexylurea, DCU, was seen within 10 minutes). The DCU was filtered and the solution was concentrated and purified on silica gel column using 50% ether in petroleum ether as eluent. HU-435 was afforded at a 28% yield. NMR (500 MHz, in $CDCl_3$): δ ppm: 6.52 (1H, s), 6.41 (1H, s), 5.20 (1H, s), 4.47 (1H, s), 4.39, (1H, s), 3.72-3.67 (7H, m), 2.85-2.40 (9H, m), 2.20-1.95, (2H, m), 1.65, (3H, s), 1.59, (3H, s), 1.30-1.22, (6H, m), 0.86, (3H, t).

Preparation of the Maleate Salt of 3-methoxy-2-((6R)-3-methyl-6-(prop-1-en-2-yl) cyclohex-2-enyl)-5-pentylphenyl 3-morpholinopropanoate (HU-436)

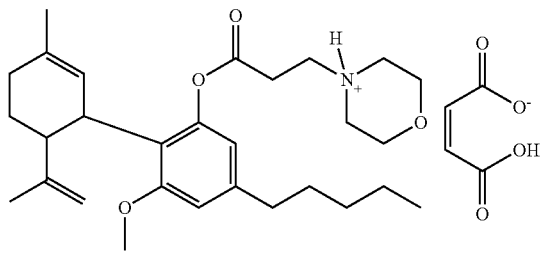

The maleate salt of HU-435 (HU-436) was prepared by stirring a solution of maleic acid (0.247 mmoles) and HU-435 (0.247 mmoles) in 20 ml 2-propanol at room temperature for 2.5 hours. The solvent was evaporated under reduced pressure and the oil obtained was crystallized from ethyl acetate and ether to afford the salt HU-436 (melting point 110-112° C.) at a yield of 80%. NMR (500 MHz, in CDCl$_3$): δ ppm: 6.53, (1H, s), 6.35, (1H, s), 6.31, (2H, s), 5.16 (1H, s), 4.44, (1H, s), 4.36, (1H, s), 3.97 (4H, m), 3.74, (3H, s), 3.35-2.6 (6H, m), 2.50-2.55 (2H, t), 1.63, (3H, s), 1.59 (3H, s), 1.30-1.22 (6H, m), 0.86, (3H, t).

In Vitro Studies

Macrophages

Peritoneal cells were harvested from C57BL/6 female mice 4 days after intra-peritoneal injection of 1.5 mL of 3% thioglycollate medium (Difco). The cells (TG macrophages) were washed with phosphate-buffered saline, re-suspended in Dulbecco's modified Eagle medium (DMEM) supplemented with 5% fetal calf serum (FCS), and plated (1.2× 10$^5$) in 96-microwell flat-bottom plates (Nunc, Roskide, Denmark). Following 2-3 h incubation at 37° C., the non-adherent cells were removed by intensive rinsing. About 95% of the adherent cells were macrophages. These cells were applied for studying TNF production in-vitro.

Raw 264.7 Macrophage Cell Line

Raw 264.7 cells, a monocytic-macrophage cell line derived from BALB/c mice, were obtained from American Type Culture collection (Rockville, Md.). The cells were cultured in Dulbecco's modified Eagle medium (DMEM) supplemented with 5% fetal calf serum (FCS) and sodium pyrovate, glutamine, and antibiotics. For activation, the cells were incubated with LPS (E. coli 1 µg/mL for 24 h, Sigma, Israel). These cells were applied for ROI and Nitric Oxide (NO) generation in-vitro.

Reactive Oxygen Intermediate (ROI) Production by Raw 264.7 Macrophages

Raw 264.7 cells were removed using a scrapper, washed, and re-suspended in Hanks balanced salt solution (without phenol red). For measurement of chemiluminescence, two luminometer tubes were each loaded with: 0.5 mL of cell suspension (5×10$^5$ cells), HU-436 (two separate doses in each tube of 40 µg/ml and 60 µg/ml), 10 µL luminol (Sigma) and 30 µL of zymosan (Sigma). The chemiluminescence in each tube was measured immediately thereafter by a luminometer (Biolumate LB 95, Berhold, Wilbad, Germany)

The results of the chmiluminescence measurements of the two tubes demonstrated an inhibition of 20% and 28% of ROI generation fallowing incubation with 40 µg/ml and 60 µg/ml HU-436, respectively.

Nitric Oxide (NO) Production by RAW 264.7 Macrophages

RAW 264.7 macrophages were treated with various doses (1-60 µg/ml) of HU-436 followed the addition of 1 µg/mL of lipopolysaccharide (LPS, E. coli, Sigma) for activation. The macrophages were then cultivated in a humid atmosphere with 5% CO$_2$ for 24 h. NO generation was determined by measuring the nitrite accumulated in the supernatants (100 µL) of the HU-436-treated macrophages as follows: An equal volume (100 µL) of Griess reagent (1% sulfanilamide, 0.1% naphthalene diamine HCl, 2% H$_3$PO$_4$) was added to each supernatant. Following 10 min of incubation at room temperature, the color production was measured at 550 nm with an ELISA reader. The concentration of nitrite was calculated according to a standard curve. The results are presented in FIG. 1 wherein inhibition of more than 50% was found fallowing incubation of the cells with 60 µg/ml HU-436.

TNF-α Determination

Figure 2:
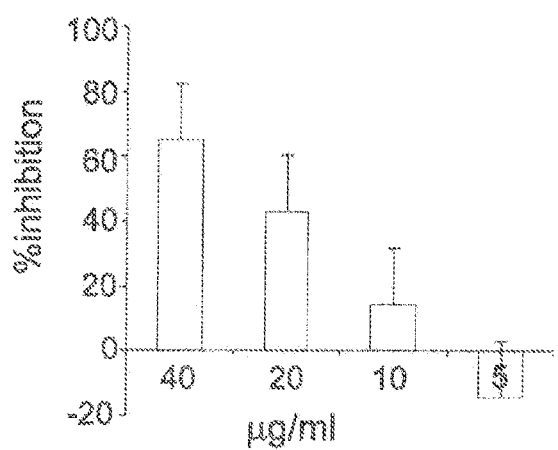
FIG. 2 shows the TNF-alpha inhibition of TG macrophages treated with doses of 5-40 μg/ml of HU-436.

TNF-α in the supernatants of TG macrophages treated with HU-436 (doses of 5-40 µL/ml) and LPS was determined by ELISA (R&D) with Ab pairs from Biosource (Camarillo, Calif.). Procedures were carried out following the manufacturer's instructions. As can be seen in FIG. 2 inhibition of more than 60% in TNF production was observed fallowing incubation of macrophages with 40 µg/ml HU-436.

In Vivo Studies

Figure 3:
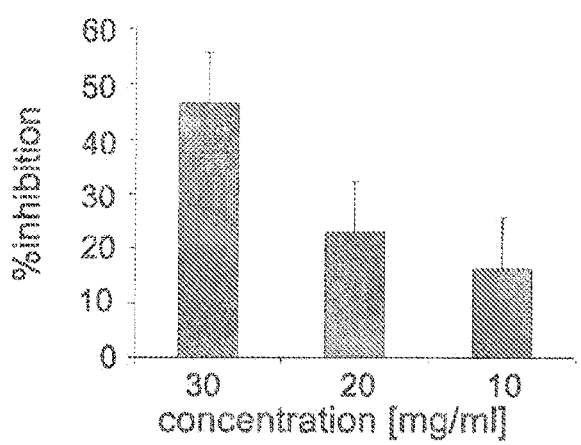
FIG. 3 shows the TNF-alpha inhibition in the serum in C57BL mice treated with HU-436 (10 mg/Kg, 20 mg/Kg and 30 mg/Kg).

Three doses of HU-436 (10 mg/Kg, 20 mg/Kg and 30 mg/Kg) were each injected to three C57BL mice together with LPS. Ninety min fallowing the injections, the mice were bled and the TNF levels in the serum were determined. As can be seen in FIG. 3, inhibition of 46% in TNF level was observed after treatment with a dose of 30 mg/Kg of HU-436. It is noted that in preliminary toxicological studies in C57BL, doses of 50 mg/Kg and 100 mg/Kg of HU-436 were found to be non-toxic.

Weight Loss Studies

Study 1

Figure 4:
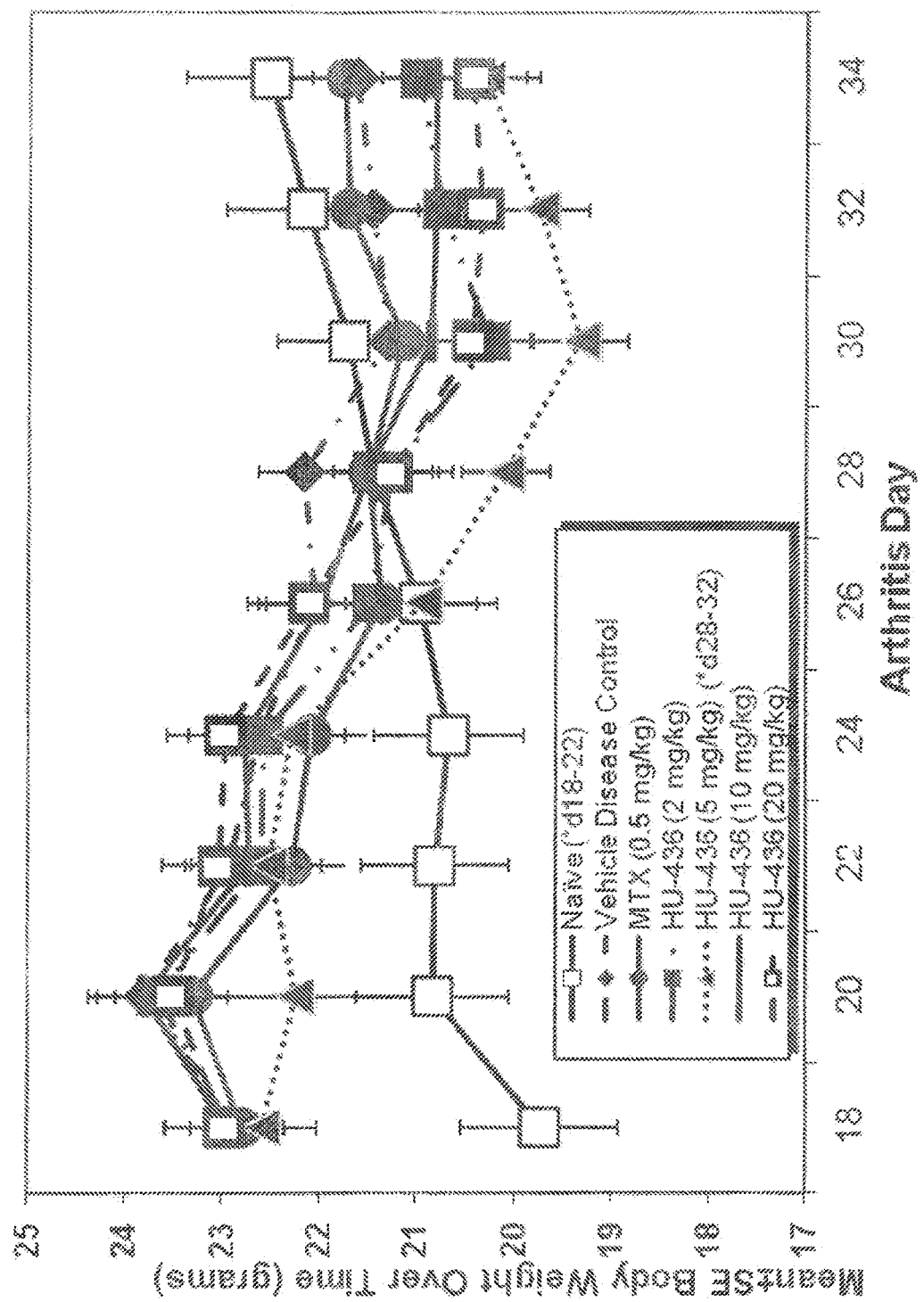
FIG. 4 shows the changes in body weight (gr) of DBA/1 male mice treated with vehicle, MTX (0.5 mg/Kg) and HU-436 (2, 5, 10 and 20 mg/Kg), in days 18-34 from injection (compared with control).
Figure 5:
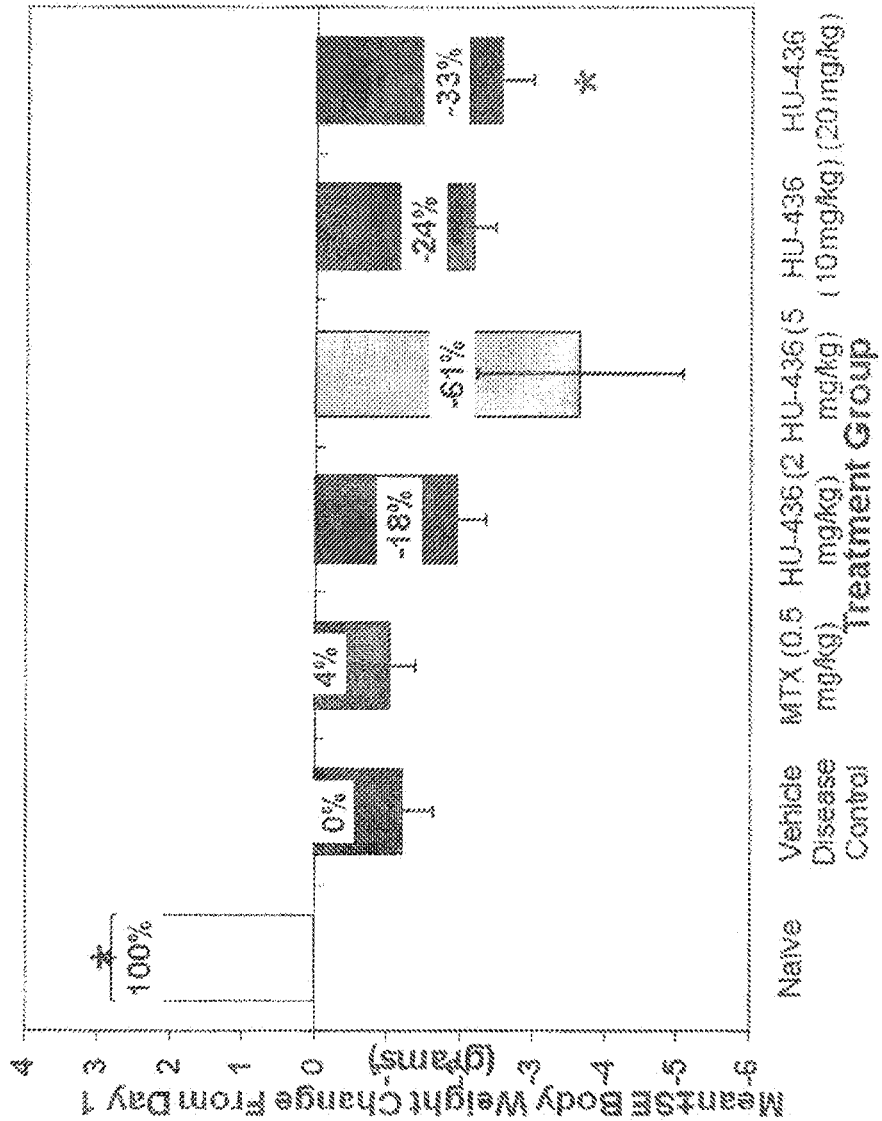
FIG. 5 shows the overall changes (34 days) in body weight (gr) of DBA/1 male mice treated with vehicle, MTX (0.5 mg/Kg) and HU-436 (2, 5, 10 and 20 mg/Kg), (compared with control).

DBA/1 male mice (6 weeks old, 20 gram, 15 mice/group) were injected Type II collagen for CIA. On day 18, the mice were injected (intra-peritoneal) with the following doses, for 16 days:
Vehicle: ethanol: chremophor: saline (1:1:18)
Methrotrexate (MTX): 0.5 mg/Kg.
HU-436: 2 mg/Kg
HU-436: 5 mg/Kg
HU-436: 10 mg/Kg
HU-436: 20 mg/Kg In addition, a control group (wherein no dose was given) was monitored for comparison. The changes in body weight (in grams) was measured daily for a period of 34 days from injection. FIG. 4 (days 18-34) and FIG. 5 (overall change from day 1 to 34), show the changes in body weight of mice over a period of 34 days from injection. A reduction of up to 61% of body weight was observed for a dose of 5 mg/Kg of HU-436 (wherein the weight gain of the control group was measured as 100% gain).

Study 2

Normal Sabra (mice 9-10 weeks old, about 32 gram, 7 mice/group) were injected (intra-peritoneal) with two doses of HU-436 (5 mg/Kg and 10 mg/Kg). The change in weight of mice was measured daily for 15 (FIG. 6) and 24 days (FIG. 7) from injection. In addition, a control group (wherein no dose was given) was monitored for comparison.

The mice were treated either with 5 mg/kg or 10 mg/kg of HU436 (ip). Mice were scored at 10 minutes 90 minutes or 180 minutes after administration. In addition to mice treated with vehicle as control, 1 mice was injected ip with 5 mg/kg CBD and scored 10 minutes later. The movements/kicking of the mice were counted and the data are presented in the attached Table 1.

The results clearly show similar locomotor pattern as measured by movement and kicking between subjects treated with HU436 as compared with control group. Additionally, it was shown that HU436 did not cause depressive activity in treated mice.

TABLE 1

| Forced Swimming test in mice: moment/kicking per minute score per minute (last 4 min) | | | | | | | | | | | |
|---|---|---|---|---|---|---|---|---|---|---|---|
| Time after placement in tank (min) | Control 1 | Control 2 | Control 3 | Control 4 | HU436 5 mg/kg | HU436 5 mg/kg | HU436 10 mg/kg | HU436 10 mg/kg | HU436 10 mg/kg | HU436 10 mg/kg | CBD 5 mg/kg |
| | | | | | 10 min after ip | 90 min after ip | 10 min after ip | 180 min after ip | | | 10 min after ip |
| 3 | 80 | 88 | 90 | 93 | 84 | 70 | 80 | 76 | 74 | 79 | 76 |
| 4 | 88 | 81 | 81 | 71 | 96 | 85 | 84 | 52 | 64 | 80 | 75 |
| 5 | 100 | 71 | 78 | 66 | 76 | 72 | 64 | 90 | 112 | 89 | 48 |
| 6 | 88 | 92 | 80 | 76 | 68 | 73 | 72 | 90 | 83 | 76 | 60 |
| Mean | 89 | 83 | 77 | 77 | 81 | 75 | 75 | 77 | 83 | 81 | 65 |

Figure 6:
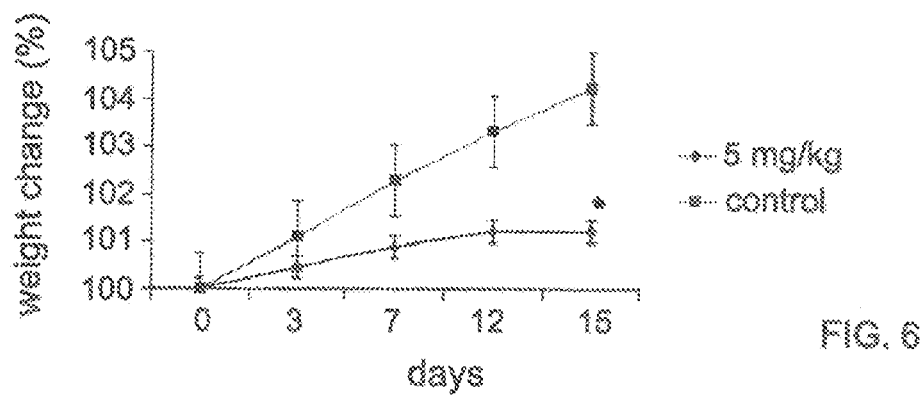
FIG. 6 shows the changes in weight (%) of Sabra mice treated with HU-436 (5 mg/Kg) over a period of 15 days (compared to control).
Figure 7:
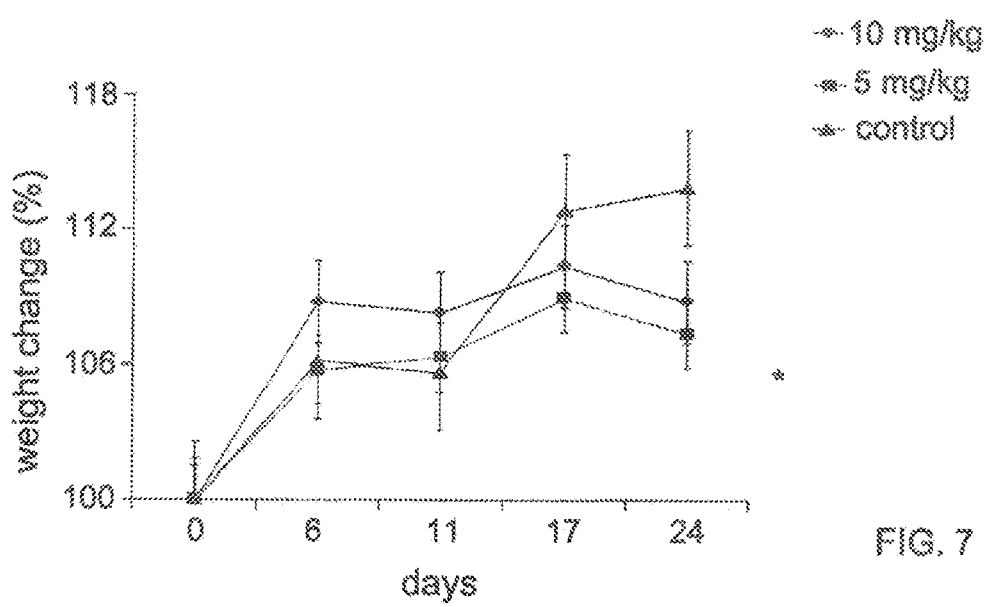
FIG. 7 shows the changes in weight (%) of Sabra mice treated with HU-436 (5 mg/Kg and 10 mg/Kg) over a period of 24 days (compared to control).

As can be seen in FIGS. 6 and 7, administration of 5 mg/Kg of HU-436 significantly decreased the changes in weight gain of mice.

Study 3

Figure 8:
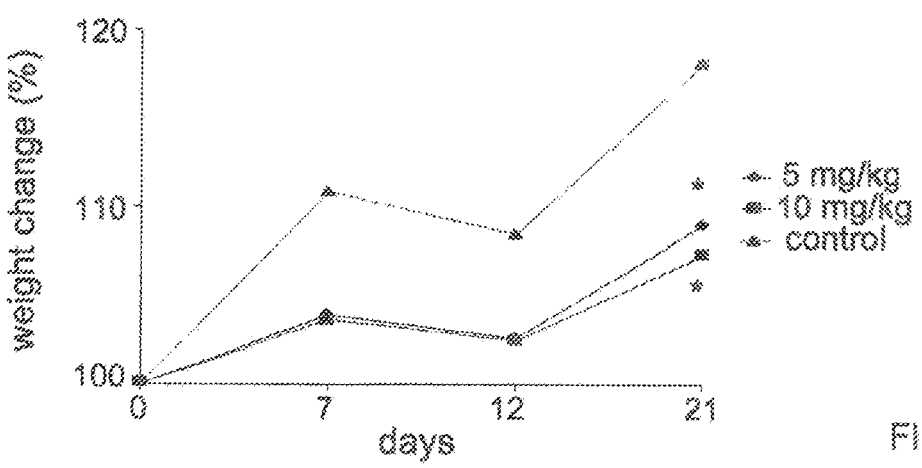
FIG. 8 shows the changes in weight (%) of SC57BL mice treated with HU-436 (5 mg/Kg and 10 mg/Kg) over a period of three weeks (compared to control).
Figure 9:
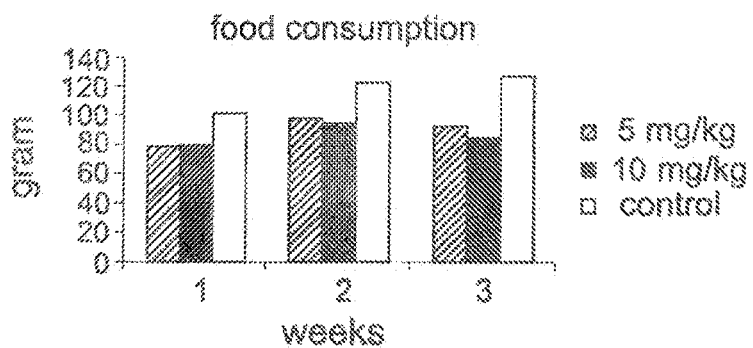
FIG. 9 shows the changes in food consumption (gr) of SC57BL mice treated with HU-436 (5 mg/Kg and 10 mg/Kg) over a period of three weeks (compared to control).

C57BL/6 mice (8-9 weeks old, 16 gram, 5 mice/group) were injected (intra-peritoneal) with two doses of HU-436 (5 mg/Kg and 10 mg/Kg). The change in weight of mice was measured weekly for three weeks (FIGS. 8 and 9) from injection. In addition, a control group (wherein no dose was given) was monitored for comparison. Both doses of HU-436 showed a significant reduction (of about 50%) in weight gain compared to the control group (see FIG. 8). A reduction in food consumption with both doses of HU-436 was observed after 1-3 weeks (FIG. 9).

Determination of Depressive Effect of HU436-Forced Swimming Test

To find out whether HU436 has depressive effects on mice behavior—a forced swimming test (FST) was adopted.

Experimental

Female sabra mice 6-8 weeks old were employed. Measurement of locomotor activity in mice movements were counted for 6 minutes.

Forced Swimming test (FST): The forced swimming test employed was essential similar to that described in ((Pettit-Demoulier et al, (2005) *Psychopharmacology* 177:245-255;)

Mice were dropped individually into a glass aquarium (height 2.5 cm, diameter 10 cm) containing 10 cm of water and their activity was monitored for 6 minutes. Of the total 6 minutes only the last 4 minutes was recorded—the first 2 minutes were considered as time for habitation.

Effect of HU-436 on Pain and Inflammation

Activity of HU-436 given orally were assayed in Sabra mice. Zymosan injected to mice left hind paw, induced inflammation, TNF (tumor necrosis factor) in the serum as well as pain. During 24 h, the inflammatory paw swelling response was assayed by caliper, whereas the pain in the hind paw, was determined by Von Frey monofiber instrument.

Methods

Sabra female, mice 6-7 weeks old, were employed. Zymosan 0.6 mgr in 40 micro-liters was injected into the left hind paw. Immediately thereafter 20 30, 50 or 100 mg/kg HU436 dissolved in olive oil, in 200 µl—was given orally. Two, six and twenty-four hours thereafter, the injected left hind paw of the mice (total 5-8 mice/treatment), were examined both for swelling (Inflammation) and pain (Von Frey). The levels of TNFα in the sera of Sabra mice were determined by Elisa, 24 hrs after HU-436 application.

Results

Inflammation

Figure 12A:
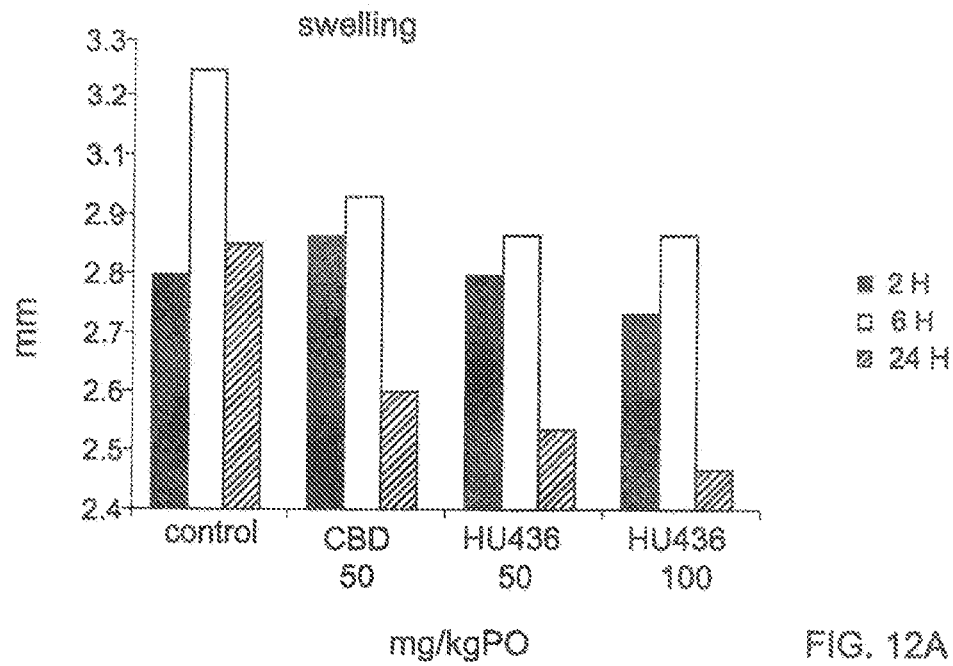
FIGS. 12A-12B shows the second swelling-inflammation (FIG. 12A) and pain (FIG. 12B) comparative results of administration of 50 and 100 mg/kg of HU436, CBD and control.
Figure 12B:
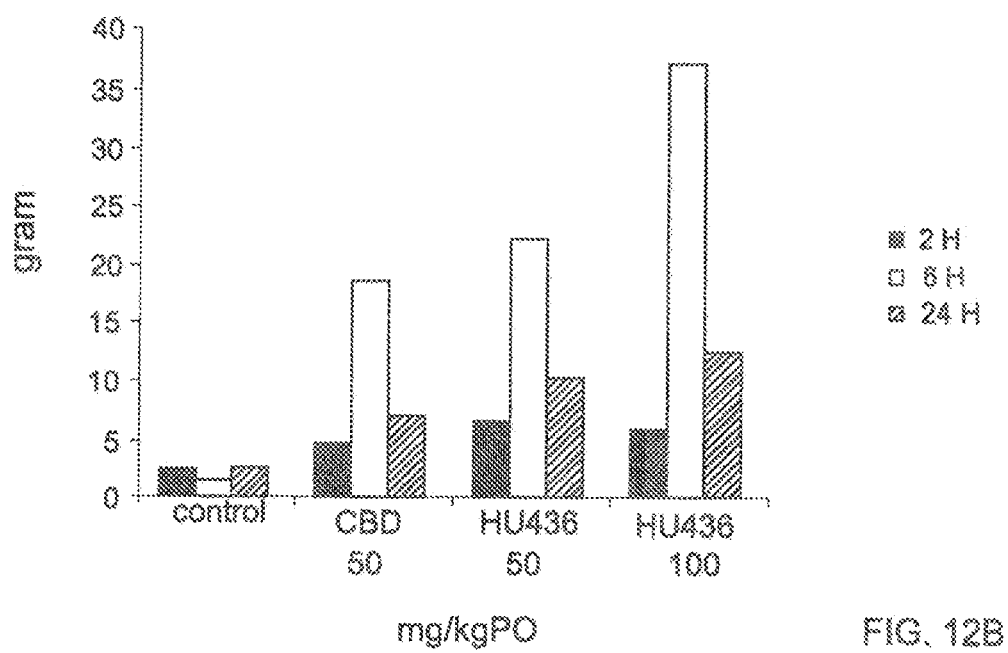
Figure 13A:
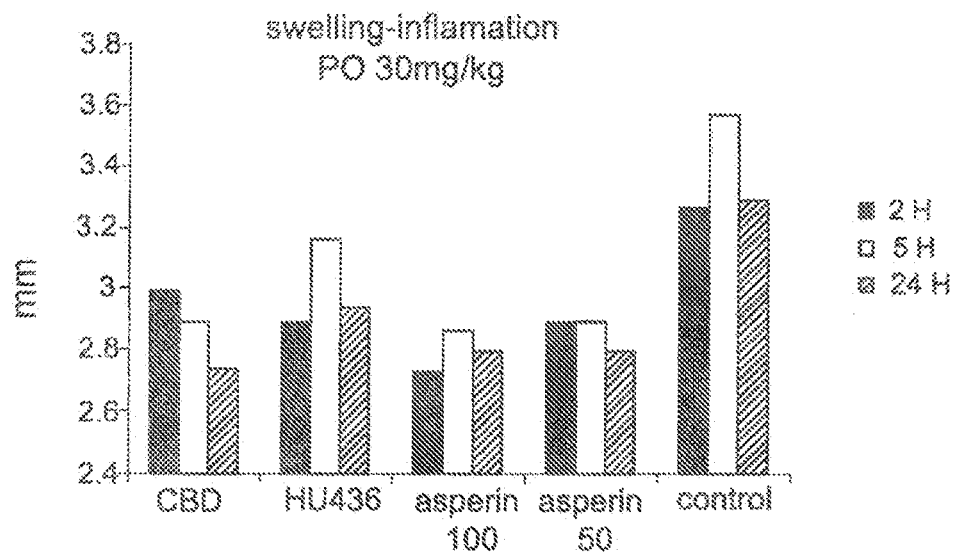
FIGS. 13A-13B shows the swelling-inflammation (FIG. 13A) and pain (FIG. 13B) comparative results of administration of 30 mg/kg of HU436, CBD, aspirin 100, aspirin 50 and control.
Figure 14A:
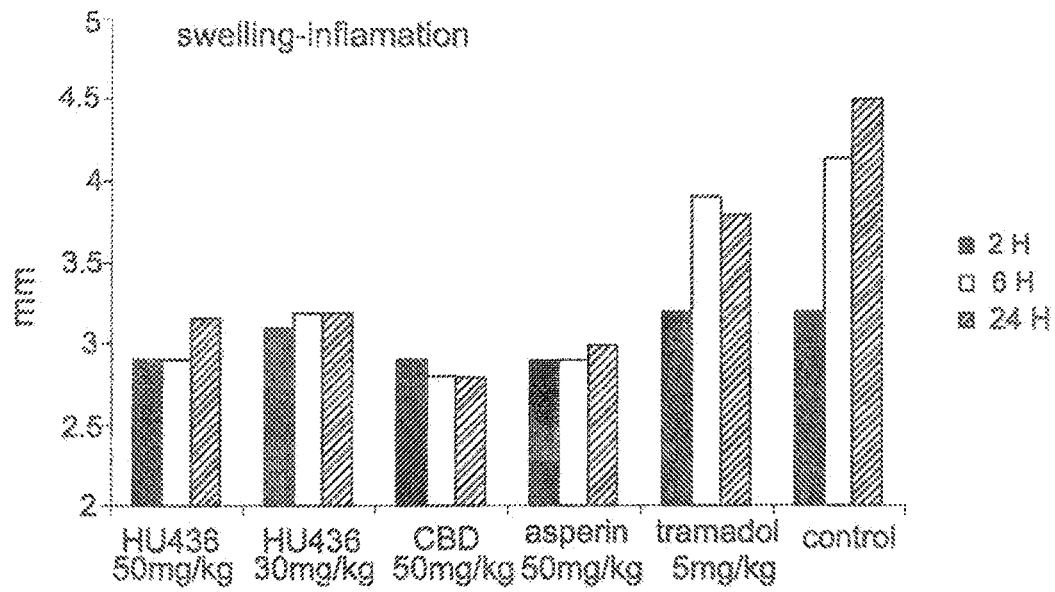
FIGS. 14A-14B shows the swelling-inflammation (FIG. 14A) and pain (FIG. 14B) comparative results of administration of HU436 30 mg/kg and 50 mg/kg, CBD 50 mg/kg, aspirin 50 mg/kg, tramadol 5 mg/kg and control.
Figure 15A:
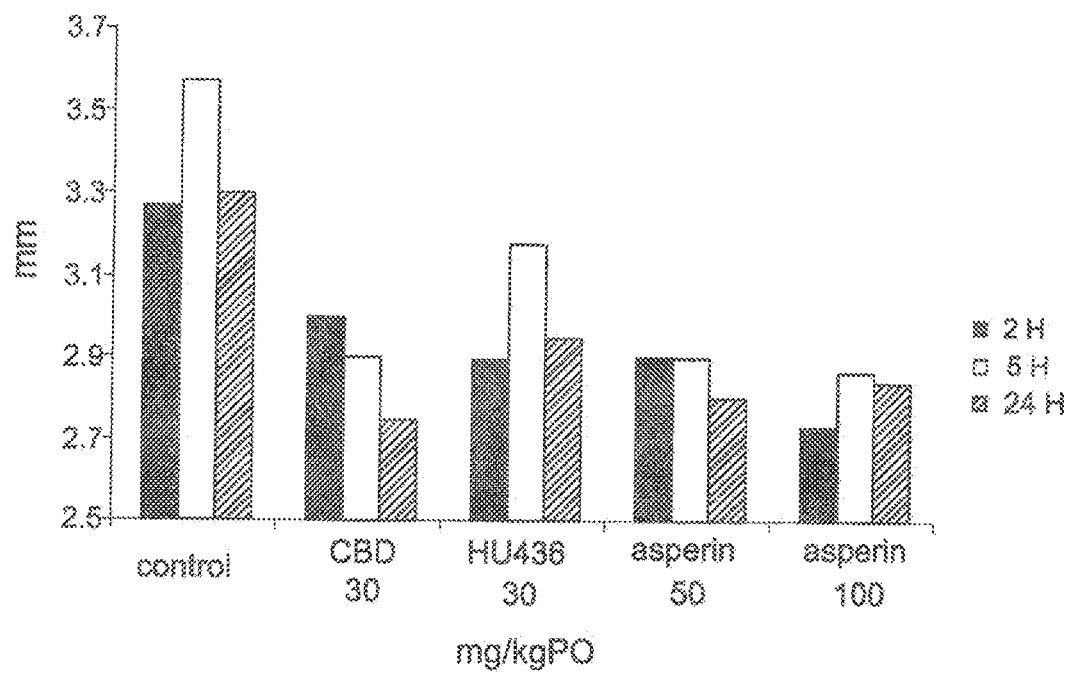
FIGS. 15A-15B shows the swelling-inflammation (FIG. 15A) and pain (FIG. 15B) comparative results of administration of HU436 30 mg/kg, CBD 30 mg/kg, aspirin 50 and 100 mg/kg, and control.

Following ip injection of 20 mg/kg HU-436 to Sabra female mice, (see FIG. 10A, 11A, 12A) reduction in inflammatory response (swelling) was observed compared to controls. When HU-436 was given orally, in doses of 30 and 50 mg/kg it reduced inflammation compared to the controls (FIGS. 13A, 14A and 15A). Cannabidiol (CBD) in all experiments was scientifically more potent than HU-436 in reducing inflammation.

TNF

Figure 16A:
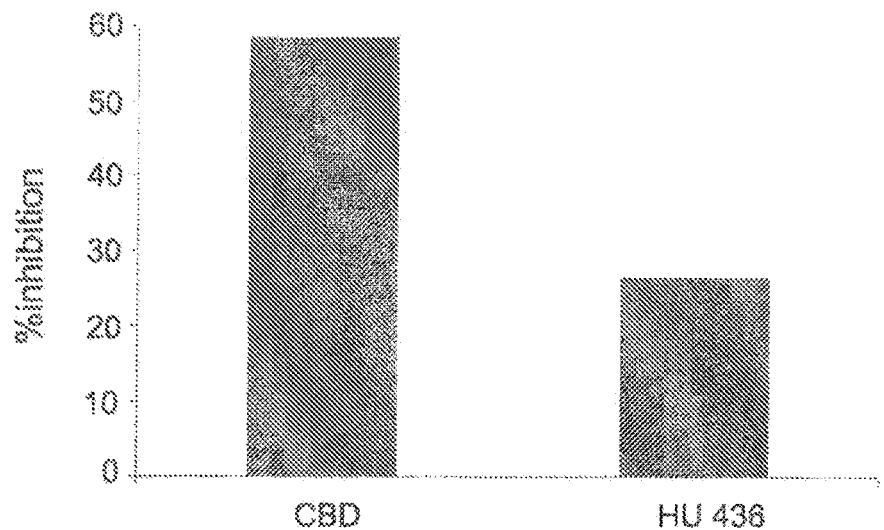
FIG. 16A-16B shows the TNFα levels of HU-436 as compared with CBD in the sera of Sabra mice.
Figure 16B:
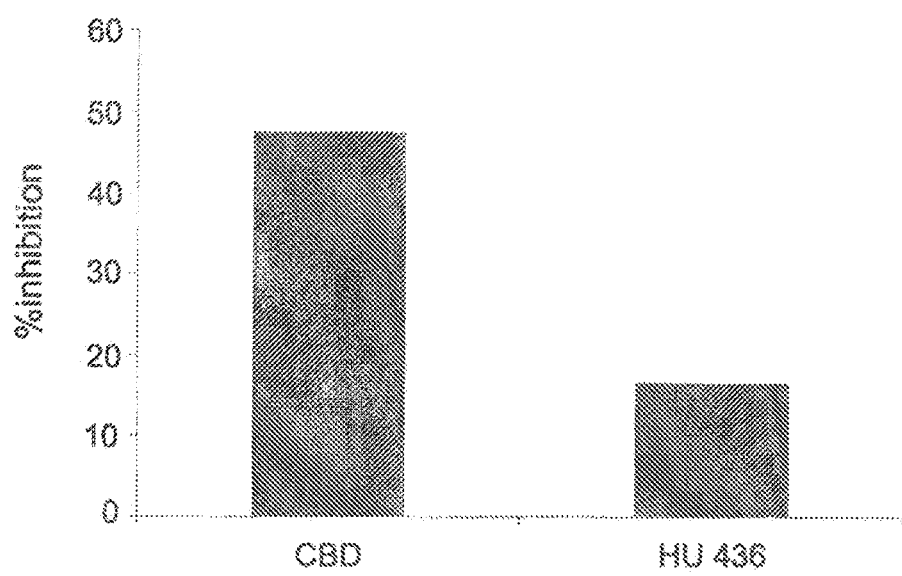

Reduction of TNFα levels in the sera of Sabra mice, fallowing application of HU-436, mirrored the inflammation extend. Suppressing TNF titers in the sera of HU-436 treated mice was smaller, up to 20%, compared to a reduction of 48-58% found in the sera of CBD-treated mice (FIGS. 16A-16B).

Pain

Pain, was assayed by employing Von-Frey monofiber instrument. The higher the log value measured, the more force (g) one has to apply to cause pain=higher analgesia is being expressed=less pain.

Data depicted in FIGS. 10-15, demonstrate a marked pain reduction of in all three HU-436 doses: 20, 30, 50 and 100 mg/kg, given orally. The higher pain reduction was detected, 24 hr after treatment, showing long lasting effect of the drug. Comparing HU-436 (30 or 50 mg/kg) effect to that of Aspirin (50 and demonstrated that HU-436 was the most potent in reducing pain for 24 hr. 50 mg/kg HU436 was more potent after 24 hr than Tremadol (5 mg/kg) given intraperitoneally. HU-436 given orally markedly decreased the pain perception in Sabra mice for an extended period of time.

Conclusions

HU-436 is a potent, long lasting anti-pain new remedy. HU-436 is more effective than Cannabidiol, Aspirin in reducing long lasting pain. HU-436 has moderate anti-inflammation properties with no observed dose response bell-shaped effect typical for other remedies in this field (where higher doses are less effective than lower doses).

What is claimed is:

1. A method for treating chronic pain in a subject in need thereof, said method comprising administering to said subject a therapeutically effective amount of a compound of the general formula (I):

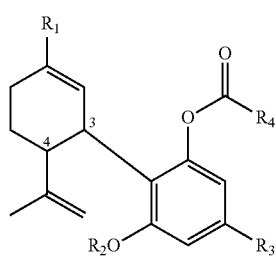

or a salt, enantiomer, diastereomer, or mixture thereof, wherein $R_1$, $R_2$ and $R_3$ are each independently a $(C_1-C_{10})$alkyl optionally substituted by at least one substituent each independently selected from the group consisting of hydroxy and halogen;

$R_4$ is a $(C_1-C_5)$alkyl substituted by a substituent of general formula (III):

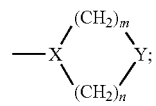

m and n are each independently is an integer selected from 0-5, wherein at least one of m or n is different than 0;
X is selected from the group consisting of N, $N^+H$, and $N^+(C_1-C_{10}$ alkyl); and
Y is —O—.

2. The method of claim 1, wherein X is N or $N^+H$.
3. The method of claim 2, wherein X is $N^+H$.
4. The method of claim 1, wherein $R_1$ and $R_2$ are each independently a $(C_1-C_5)$alkyl.
5. The method of claim 1, wherein $R_3$ is a $(C_4-C_{10})$alkyl.
6. The method of claim 1, wherein the substituents on positions 3 and 4 of said compound have a cis configuration.
7. The method of claim 6, wherein the conformation of the substituents on positions 3 and 4 of said compound are equatorial: axial or axial: equatorial.
8. The method of claim 1, wherein the substituents on positions 3 and 4 of said compound have a trans configuration.
9. The method of claim 8, wherein the conformation of the substituents on positions 3 and 4 of said compound are equatorial: equatorial or axial: axial.
10. The method of claim 1, wherein said compound is devoid of affinity to a CB receptor.
11. The method of claim 1, wherein said compound is of the formula:

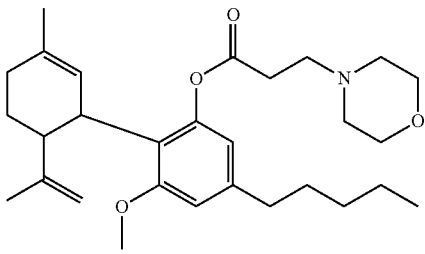 [SMILES: C=C(C)C1CCC(C)=CC1c1c(OC)cc(CCCCC)cc1OC(=O)CCN1CCOCC1]

or a salt, enantiomer, diastereomer, or mixture thereof

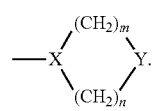

12. The method of claim 1, wherein said salt is the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, or pamoate salt of said compound.

* * * * *

UNITED STATES PATENT AND TRADEMARK OFFICE
CERTIFICATE OF CORRECTION

| | | |
|---|---|---|
| PATENT NO. | : 11,149,014 B2 | Page 1 of 3 |
| APPLICATION NO. | : 16/274107 | |
| DATED | : October 19, 2021 | |
| INVENTOR(S) | : Gallily et al. | |

It is certified that error appears in the above-identified patent and that said Letters Patent is hereby corrected as shown below:

In the Drawings

Figure 10A:
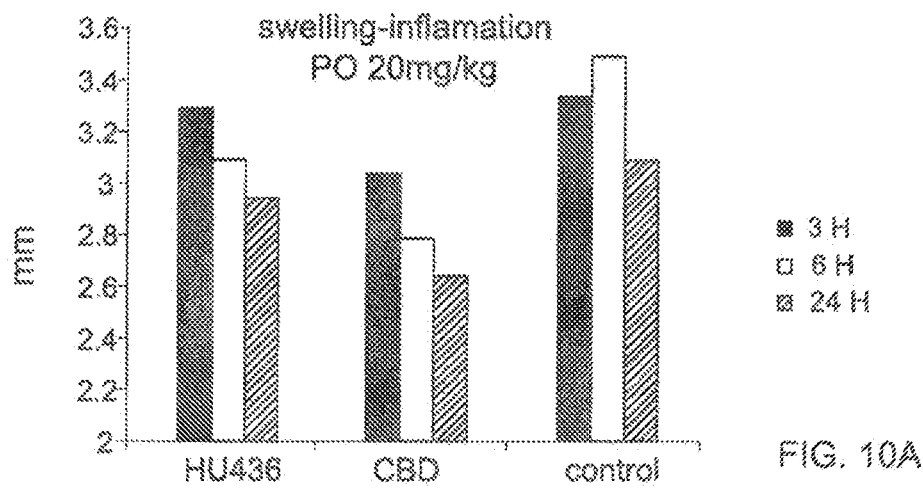
FIGS. 10A-10B shows the first swelling-inflammation (FIG. 10A) and pain (FIG. 10B) comparative results of administration of 20 mg/kg of HU436, CBD and control.
Figure 10B:
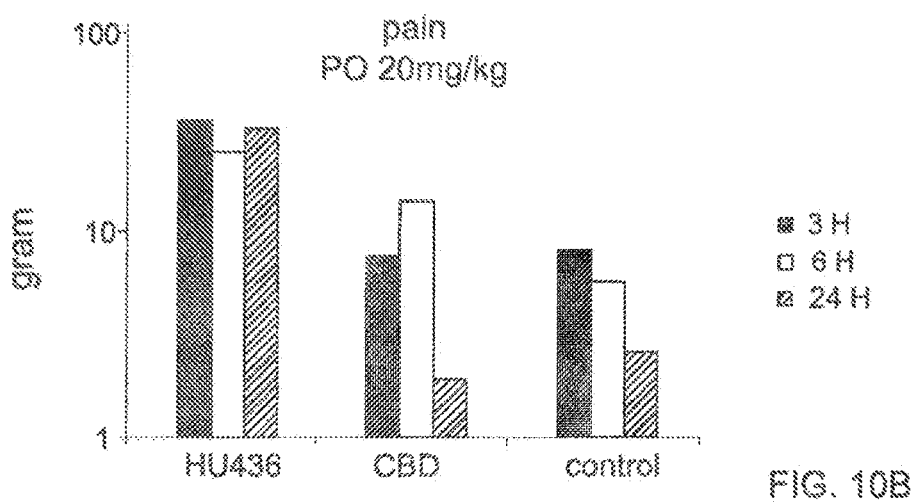

On Sheet 5 of 11, FIG. 10A, Line 1, delete "inflamation" and insert --inflammation--.

Figure 11A:
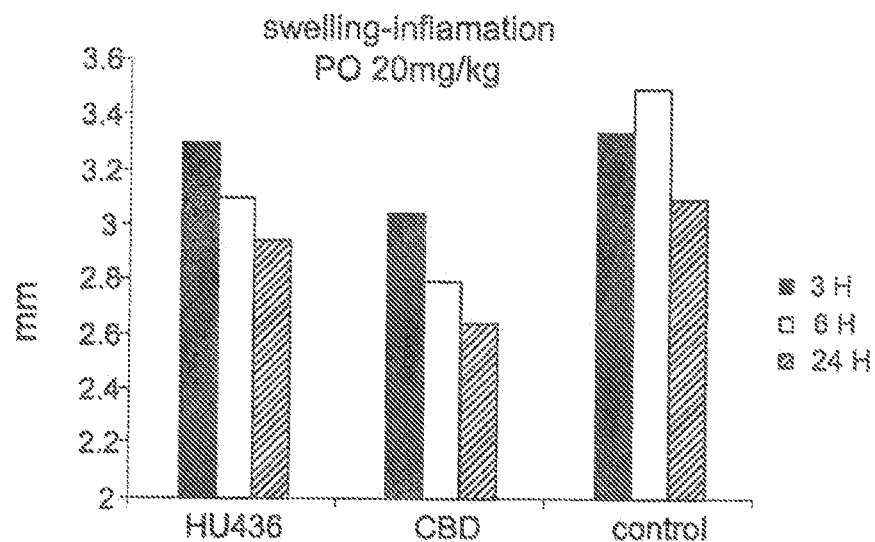
FIGS. 11A-11B shows the second swelling-inflammation (FIG. 11A) and pain (FIG. 11B) comparative results of administration of 20 mg/kg of HU436, CBD and control.
Figure 11B:
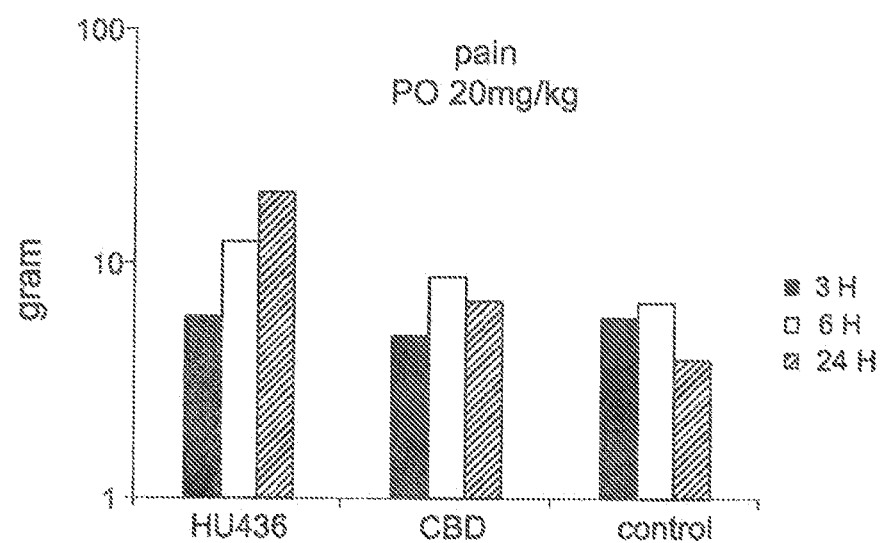

On Sheet 6 of 11, FIG. 11A, Line 1, delete "inflamation" and insert --inflammation--.

On Sheet 8 of 11, FIG. 13A, Line 1, delete "inflamation" and insert --inflammation--.

On Sheet 8 of 11, FIG. 13A, x-axis, Line 1, delete "asperin asperin" and insert --aspirin aspirin--.

Figure 13B:
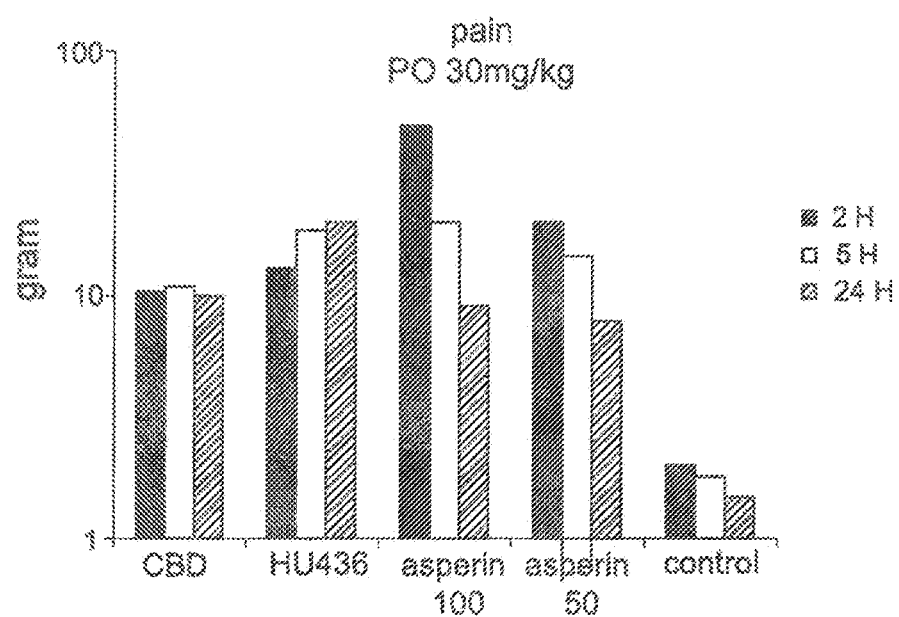

On Sheet 8 of 11, FIG. 13B, x-axis, Line 1, delete "asperin asperin" and insert --aspirin aspirin--.

On Sheet 9 of 11, FIG. 14A, Line 1, delete "inflamation" and insert --inflammation--.

On Sheet 9 of 11, FIG. 14A, x-axis, Line 1, delete "asperin" and insert --aspirin--.

Figure 14B:
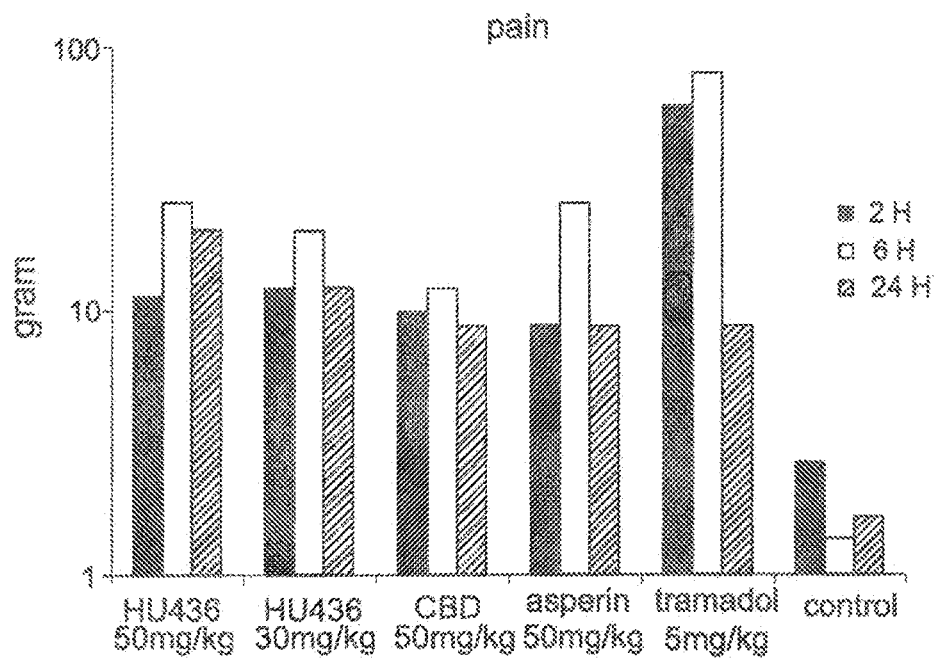

On Sheet 9 of 11, FIG. 14B, x-axis, Line 1, delete "asperin" and insert --aspirin--.

On Sheet 10 of 11, FIG. 15A, x-axis, Line 1, delete "asperin asperin" and insert --aspirin aspirin--.

Figure 15B:
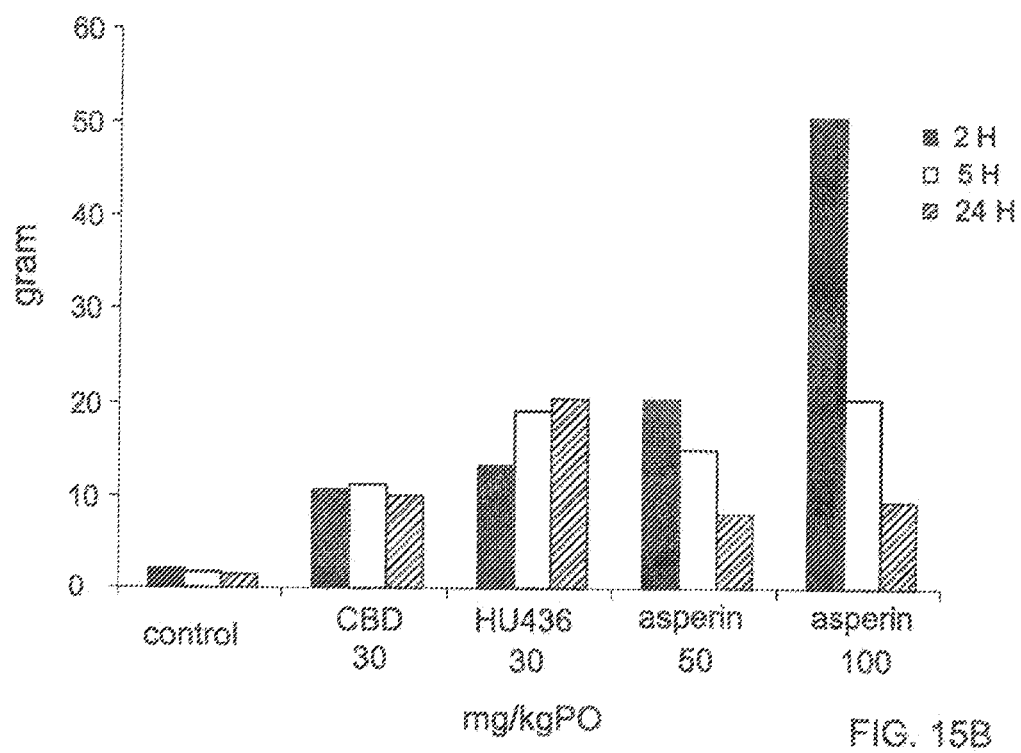

On Sheet 10 of 11, FIG. 15B, x-axis, Line 1, delete "asperin asperin" and insert --aspirin aspirin--.

In the Specification

In Column 1, Line 38 (Approx.), delete "IL-1a" and insert --IL-1α--.

In Column 1, Line 46, delete "Behay." and insert --Behav.--.

In Column 2, Line 3, delete "$C_1$-$C_{10}$" and insert --$C_1$-$C_{10}$ alkyl, $C_2$-$C_{10}$--.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,149,014 B2

In Column 2, Line 26 (Approx.), delete "$N^+(C_1-C_{10}alkyl);$" and insert --$N^+(C_1-C_{10}$ alkyl);--.

In Column 2, Line 27 (Approx.), delete ""$C_1-C_{10}alkyl$"" and insert --$C_1-C_{10}$ alkyl"--.

In Column 3, Line 16 (Approx.), delete "heterocylic" and insert --heterocyclic--.

In Column 3, Lines 18-19 (Approx.), delete "hetereocyclic" and insert --heterocyclic--.

In Column 3, Line 19 (Approx.), delete "heterocylic" and insert --heterocyclic--.

In Column 3, Lines 21-22 (Approx.), delete "hetereocyclic" and insert --heterocyclic--.

In Column 3, Line 42 (Approx.), delete "glucaronate," and insert --glucuronate,--.

In Column 3, Lines 43-44 (Approx.), delete "benzensulfonate," and insert --benzenesulfonate,--.

In Column 4, Line 49 (Approx.), delete "(axial" and insert --axial--.

In Column 5, Line 62, delete "invention" and insert --invention.--.

In Column 10, Line 26 (Approx.), delete "FIG." and insert --FIGS.--.

In Column 10, Line 50 (Approx.), delete "(prop-1" and insert --(prop-l--.

In Column 11, Line 2, delete "yI) cyclohex" and insert --yI)cyclohex--.

In Column 11, Line 40, delete "Roskide," and insert --Roskilde,--.

In Column 11, Line 53, delete "pyrovate," and insert --pyruvate,--.

In Column 12, Line 2, delete "Berhold, Wilbad," and insert --Berthold, Wildbad,--.

In Column 12, Line 2, delete "Germany)" and insert --Germany).--.

In Column 12, Line 3, delete "chmiluminescence" and insert --chemiluminescence--.

In Column 12, Line 5, delete "fallowing" and insert --following--.

In Column 12, Line 25, delete "fallowing" and insert --following--.

In Column 12, Line 36, delete "fallowing" and insert --following--.

In Column 12, Line 41, delete "fallowing" and insert --following--.

In Column 12, Line 57, delete "chremophor:" and insert --cremophor:--.

CERTIFICATE OF CORRECTION (continued)
U.S. Pat. No. 11,149,014 B2

In Column 12, Line 58, delete "Methrotrexate" and insert --Methotrexate--.

In Column 13, Line 62, delete "255;)" and insert --255).--.

In Column 14, Line 44 (Approx.), delete "200 µI-" and insert --20 µI- --.

In Column 14, Line 56, delete "FIG." and insert --FIGS.--.

In Column 14, Line 67, delete "fallowing" and insert --following--.

In Column 15, Line 21, delete "Tremadol" and insert --Tramadol--.

In the Claims

In Column 16, Line 61, Claim 12, delete "glucaronate," and insert --glucuronate,--.

In Column 16, Line 62, Claim 12, delete "benzensulfonate," and insert --benzenesulfonate,--.